US006107095A

United States Patent [19]
Mazurkiewicz

[11] Patent Number: 6,107,095
[45] Date of Patent: Aug. 22, 2000

[54] METHOD FOR INTRODUCING SUBSTANCES INTO LIVING CELLS AND TISSUES

[76] Inventor: Marian Mazurkiewicz, P.O. Box 1753, Rolla, Mo. 65401

[21] Appl. No.: 08/157,406

[22] Filed: Nov. 26, 1993

[51] Int. Cl.[7] .......................... C12N 15/74; C12N 15/80; C12N 15/82; C12N 15/85

[52] U.S. Cl. .......................... 435/470; 435/455; 435/459; 435/468; 435/471; 800/293; 222/54; 239/222.17

[58] Field of Search ............................... 435/172.1, 172.3, 435/455, 459, 468, 470, 471; 935/52, 53, 85; 222/54; 239/222.17; 800/293

[56] References Cited

U.S. PATENT DOCUMENTS

| 4,945,050 | 7/1990 | Sanford et al. | 435/172.1 |
|---|---|---|---|
| 5,036,006 | 7/1991 | Sanford et al. | 435/170.1 |
| 5,141,131 | 8/1992 | Miller et al. | 222/54 |
| 5,152,458 | 10/1992 | Curtis | 239/222.17 |
| 5,240,842 | 8/1993 | Mets | 435/172.3 |

OTHER PUBLICATIONS

"Microprojectile Bombardment: A method for the Production of Transgenic Cereal Crop Plants And The Functional Analaysis of Genes", Fionnuala Morrish et al., *Transgenic Plants—Fundamentals and Applications*, Ed. Andrew Hiatt, pp. 133–149, 158.

*Primary Examiner*—David T. Fox
*Attorney, Agent, or Firm*—Armstrong Teasdale LLP

[57] ABSTRACT

A method of introducing a biological substance into living target cells, the method comprising dispersing a liquid containing the biological substance into microdroplets and propelling the microdroplets toward to the target cells.

3 Claims, 3 Drawing Sheets

METHOD FOR INTRODUCING SUBSTANCES INTO LIVING CELLS AND TISSUES

BACKGROUND OF THE INVENTION

This invention relates to a method of introducing substances into living cells or tissues without killing those cells or tissues.

Biologists often need to introduce into living cells or tissues a wide range of substances which are normally excluded from the cell by the cell walls and outer membranes. These substances include biological stains, proteins, nucleic acids, organelles, chromosomes, and nuclei. One application of central importance is the introduction of genetic materials into cells for the purpose of genetic engineering.

Sanford et al., U.S. Pat. No. 4,945,050, (incorporated herein by reference), discloses a method of transporting substances into living cells and tissues, and an apparatus therefor. Generally, the method disclosed in Sanford et al. involves propelling inert or biologically active particles at cells at a sufficient speed that the particles penetrate the surface of the cells and become incorporated into the interior of the cells. These particles thus provide a vector for introducing substances into living cells. Sanford et al. discloses various apparatus for accelerating the particles to a predetermined speed and propel the particles toward a target.

While the Sanford et al. method is effective, it has a number of shortcomings. The literature reports that in micro projectile bombardment there is poor control over size, aggregation, coating, quantity, dispersal and velocity of particles. A principal shortcoming of Sanford, et al. is that the method is not particularly efficient. It is believed that at least some of the weakly adherent coating of genetic material is lost in the process of accelerating the particles to the speed required to penetrate the cell walls. It is also believed that at least some of the coating of genetic material is "wiped" off the particles as they penetrate the cell walls. Another shortcoming of Sanford, et al. is that it is not satisfactory for introducing RNA, which is unstable, into cells. It is difficult to coat particles with RNA without altering or destroying the RNA. The inventor also believes that biological material, such as DNA is better able to withstand the acceleration and other forces encountered in the introduction into living cells, when in a liquid droplet, rather than on a solid particle. Still another shortcoming of Sanford, et al. is the physical disruption of the cell caused by the particle, and the heat generated by the impact of the particle on the cell. Finally, the ability to adjust particle energy is limited to Sanford, et al., making adjustments to different cell type difficult.

SUMMARY OF THE INVENTION

Generally, according to the method of this invention, biological material in liquid form, or in a liquid solution or suspension (all hereinafter referred to as a biological liquid) is dispersed into microdroplets and propelled against cells to inoculate the cells with the biological liquid. This method can be implemented in a number of ways.

One way of dispersing a biological liquid into microdroplets and propelling these microdroplets toward target cells employs a centripetal acceleration, which has a revolving vessel, driven by an air turbine or other means. Small orifices in the periphery of the vessel disperse the liquid in the vessel into microdroplets, which are propelled radially outwardly. Through adjustment of rotation speed and standoff distance, microdroplet size and speed can be controlled to provide optimum conditions for introducing biological material into the target cells.

A second way of dispersing a biological liquid into microdroplets and propelling these microdroplets toward target cells employs a cylinder with a small-orifice nozzle and a high pressure plunger to disperse liquid ejected from the nozzle into microdroplets. Through adjustment of the size and shape of the nozzle, the pressure applied by the plunger, and the standoff distance, microdroplet size and speed can be controlled to provide optimum conditions for introducing the biological liquid into the target cells.

A third way of dispersing a biological liquid into microdroplets and propelling these microdroplets toward target cells comprises a high speed revolving rotor having a plurality of blades. Droplets of liquid impacted by the rotor blades are dispersed into microdroplets, and propelled toward the target cells. Through adjustment of rotor speed, droplet density, and the standoff distance, microdroplet size and speed can be controlled to provide optimum conditions for introducing biological material into the target cells.

A fourth way of dispersing a biological liquid into microdroplets and propelling these microdroplets toward target cells employs a micro projectile having a nozzle filled with the biological liquid. The micro projectile is accelerated forward and stopped, dispersing the biological liquid into microdroplets, and propelling the microdroplets toward the target cells. Through adjustment of the nozzle size, micro projectile speed, and standoff distance, microdroplet size and speed can be controlled to provide optimum conditions for introducing biological material into the target cells.

In the present invention, biological material is dissolved within the droplet and is not a coating on the surface that can be lost through mechanical action in accelerating the droplet, nor in the process of penetrating the cell wall. Thus, the present invention can more efficiently deliver biological material to the cells. Furthermore, because the biological material is dissolved in a liquid, and preferably in water, the genetic material is protected. It is expected that even RNA can be introduced into cells with the method of the present invention. It is believed that the droplets will not be as physically disruptive to cells as particles either during the process of penetration nor thereafter. Moreover, the penetration of a droplet into the cells is expected to generate less heat than the penetration of a particle, and the liquid can be cooled to further reduce effects of heating of the cell. Finally, the method of the present invention provides a number of ways to control droplet energy and thus cell penetration. The liquid pressure, nozzle shape and size, and standoff distance can all be adjusted to optimize the delivery of genetic material. The surface tension of the droplets can be adjusted, for example, through the addition of alcohols, detergents, or other substances, to control the droplets' penetration of the cells. Appropriate buffer composition will assure stability of biological material in droplets. Low temperature of droplet will further extend the stability of biological material to be introduced. There will be no contamination of cells with solid particles, which might cause death of cells. Concentration of biological material in droplets can be easily and widely adjusted. The method provides low cost, efficient delivery of biological material into cells or tissues.

Thus, the method of the present invention provides a method of introducing biological materials into cells or tissues with less chances of destroying them. The method avoids the difficulties of conventional cell uptake methods and the difficulties of using particles to bombard the cells.

These and other features and advantages will be in part apparent and in part pointed out hereafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

The method of this invention introduces a biological substance into target cells by taking the biological substance either in liquid form, or in a liquid solution or suspension, and dispersing this biological liquid into microdroplets sufficiently small to alter the cells without destroying them, and propelling these microdroplets toward the target cells with sufficient speed that the microdroplets penetrate the target cells. The microdroplets must be sufficiently small to penetrate the cell without destroying the cell, yet sufficiently large that sufficient kinetic energy can be imparted to the microdroplets to penetrate the cell walls. Typical cell diameters range from about $10\mu$ to about $2000\mu$. In general, a droplet size of about $\frac{1}{10}$ to $\frac{1}{4}$ of the diameter of the cell are suitable for introducing biological substances into the cells. The dispersing and propelling of the microdroplets biologic fluid can be implemented in several different ways.

Figure 1:
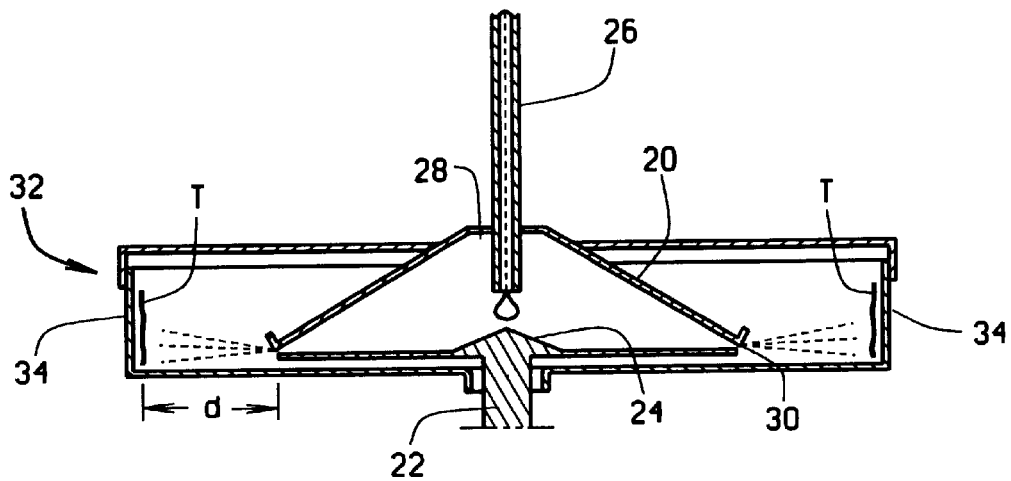
FIG. 1 is vertical cross-sectional view of a centripetal accelerator for dispersing and propelling microdroplets of biological liquid according to the first embodiment of this invention.
Figure 2:
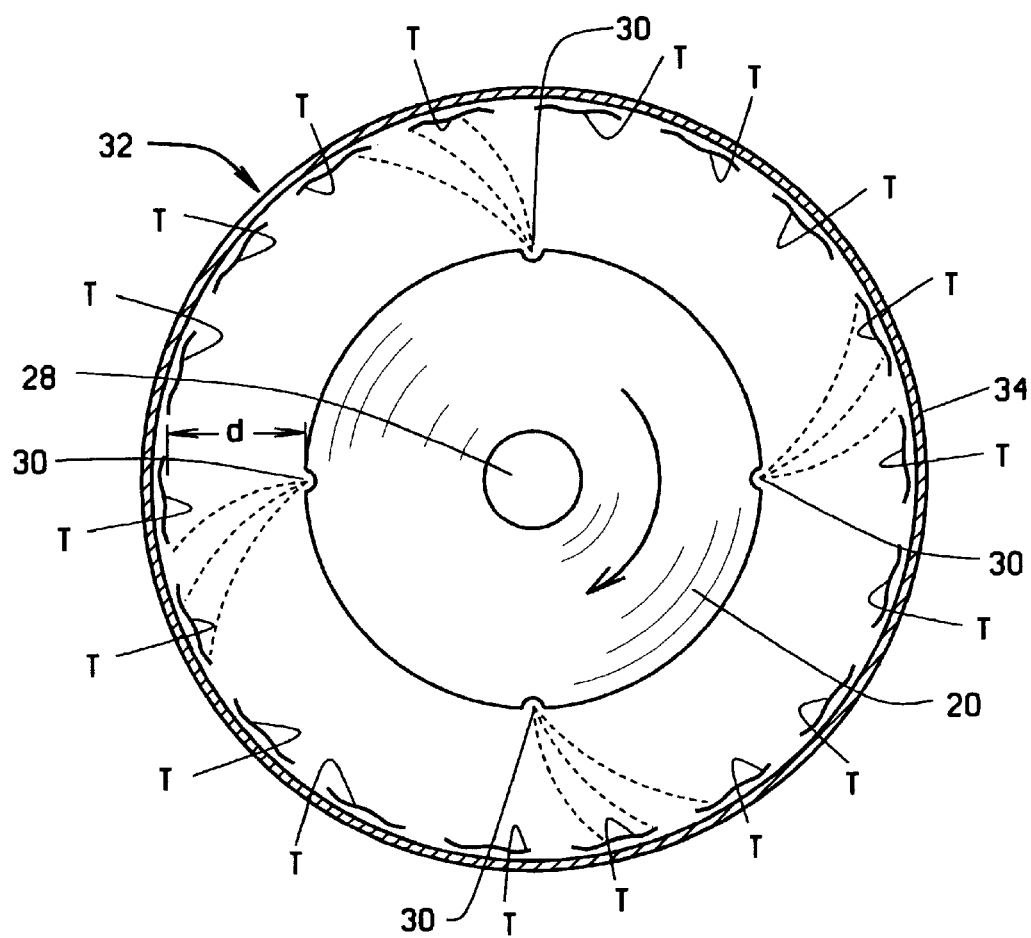
FIG. 2 is a top plan view of the centripetal accelerator of the first embodiment.

A first embodiment of an apparatus for dispersing a biological liquid into microdroplets and propelling the microdroplets is shown in FIGS. 1 and 2. As shown in FIGS. 1 and 2, a hollow, generally frustoconical vessel 20 is mounted on a rotor 22 for high speed rotation. The rotor 22 may be driven, for example, by an air turbine (not shown). There is a conical land 24 inside the vessel 20, at the center. Biological liquid is delivered via a pipette 26 through the open top 28 of the vessel 20, to the conical land 24. Through the rotation of the vessel 20, the biological liquid is accelerated radially outwardly through openings 30 in the periphery of the vessel 20, dispersing the liquid into microdroplets, and propelling the microdroplets radially outwardly. The vessel 20 is contained in a housing 32, and the target cells T are mounted in holders 34 around the interior circumference of the housing 30. The size and the speed of the microdroplets can be controlled by controlling the speed of rotation of the vessel 20, and the standoff distance d, which is the distance between the openings 30 in the periphery of the vessel 20 and the holders 34 on walls of the housing 32.

Figure 3:
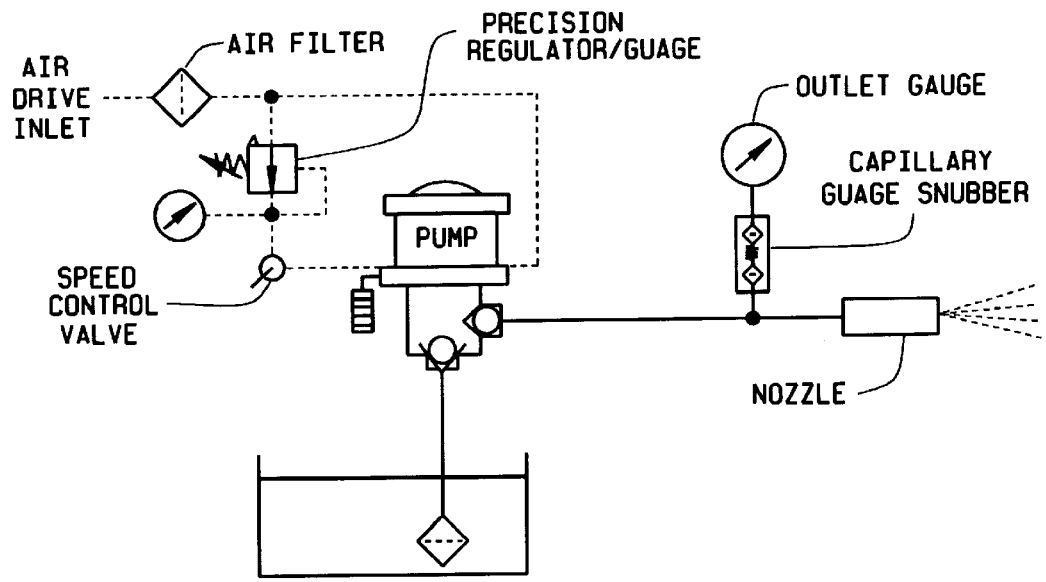
FIG. 3 is a schematic view of a high pressure system for dispersing and propelling microdroplets of biological liquid according to a second embodiment of this invention.
Figure 4:
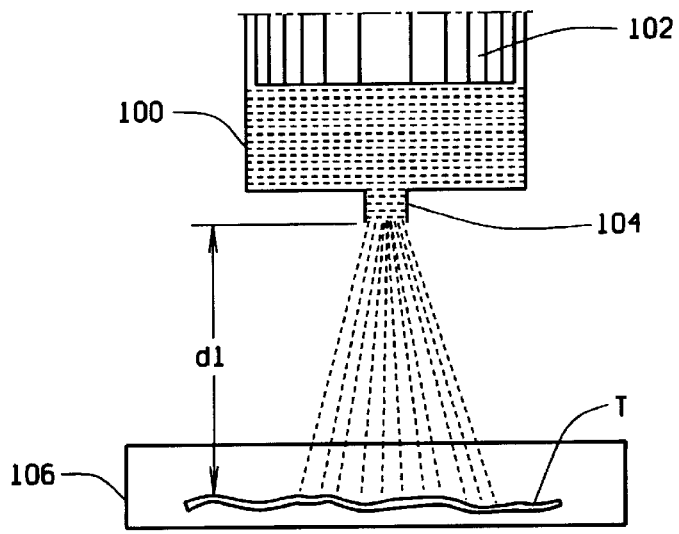
FIG. 4 is a schematic view of the cylinder and nozzle of the high pressure system of the second embodiment.

A second embodiment of an apparatus for dispersing a biological liquid into microdroplets and propelling the microdroplets is shown in FIGS. 3 and 4. As shown in FIG. 4, biological liquid in cylinder 100 under pressure from piston 102, is ejected through nozzle 104 dispersing the biological liquid into microdroplets and propelling the microdroplets toward target cells on a holder 106. The size and speed of the microdroplets is a function of the nozzle size and configuration, the pressure in the cylinder 100, and the standoff distance $d_1$ which is the distance between the outlet of nozzle 104 and the target cells on the holder 106.

Figure 5:
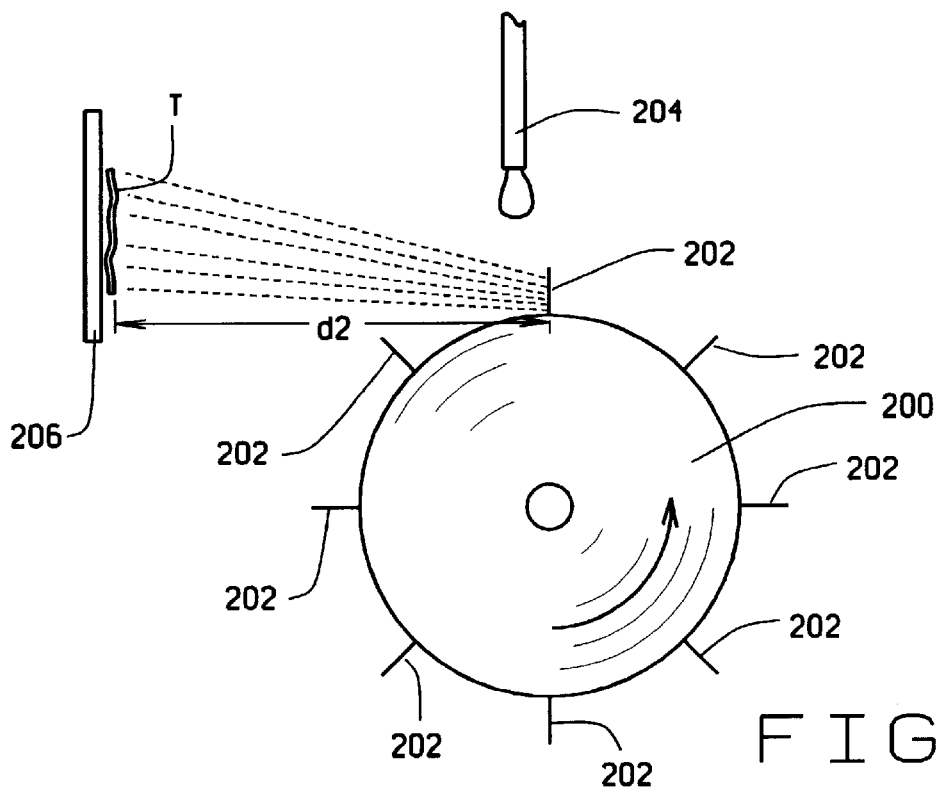
FIG. 5 is a schematic view of a rotor for dispersing and propelling microdroplets of biological liquid according to a third embodiment of this invention.

A third embodiment of an apparatus for dispersing and propelling a biological liquid into microdroplets is shown in FIG. 5. As shown in FIG. 5, a rotor 200 having radial blades 202 is rotated at high speed. Drops of the biological liquid are delivered from pipette 204 into the path of the blades 202 on the rotor 200. The blades 202 impact the drops, dispersing the liquid into microdroplets and propelling the microdroplets toward target cells on a holder 206. The size and speed of the microdroplets is a function of the speed of the rotor and the standoff distance $d_2$ from the point where the droplets are struck by the blades and the target cells.

Figure 6:
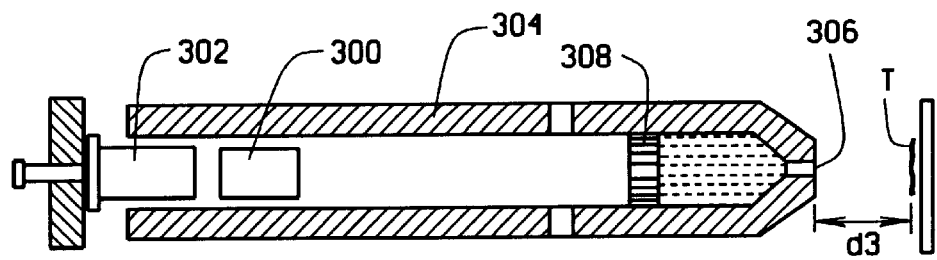
FIG. 6 is a schematic view of a microprojectile and firing apparatus for dispersing and propelling microdroplets of biological liquid according to a fourth embodiment of this invention.
Figure 7:
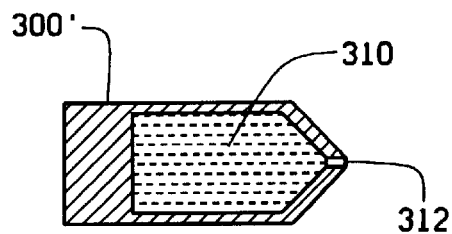
FIG. 7 is an enlarged longitudinal cross-sectional view of the micro projectile employed in the fourth embodiment.

A fourth embodiment of an apparatus for dispersing and propelling a biological liquid into microdroplets is shown in FIG. 6. As shown in FIG. 6, a microprojectile 300 is fired with a charge 302 through a tube 304. There is a nozzle 306 in the forward end to the tube 304. A supply of biological liquid is held in the front of the tube 304 with a piston 308. The projectile 300 impacts the piston 308, ejecting biological liquid through the nozzle 306, dispersing the liquid into microdroplets and propelling the droplets forward toward target cells T on a holder 314. Alternatively, as shown in FIG. 7, the micro projectile 300' can have a chamber 310, containing the biological liquid. The microprojectile 300' is propelled forward in the tube 304. The forward end of the tube 304 is closed, except for a nozzle 312 therethrough. The microprojectile 300 travels forward in the tube 304, and is stopped at the closed forward end 306 of the tube. The biological liquid in the microprojectile is ejected through the nozzle 312 of the microprojectile 300' and through the nozzle 306 of the tube 304, dispersing the liquid into microdroplets and propelling the droplets forward toward target cells T on a holder 314. The size and speed of the droplets is a function of the speed of the microprojectile 300, the size and shapes of the nozzles 306 and 312, and the standoff distance $d_3$ between the outlet of the nozzle 306 and the cells T on the holder 314.

The ability to disperse a liquid into microdroplets of appropriate size and kinetic energy to impact and enter a living cell has been demonstrated. For example, a sheet of lead was used as a target for the dispersion of microdroplets of water. The visible pitting in the lead sheet shows a range of sizes on the order of $1\mu$ to $10\mu$, can be created. These are of sufficient size to penetrate a cell without destroying it. The depth of the pitting demonstrates that sufficient kinetic energy can be imparted to microdroplets to penetrate cells. By controlling the standoff distances, the energy of the microdroplets impacting the cells can be reduced to an appropriate level that allows the microdroplets to penetrate the cells without destroying them.

OPERATION

In operation, a biological substance, for example, genetic material for altering the genetic structure of a plant, is isolated. A biological liquid is made from the genetic material with water or other suitable liquid. The biological liquid is dispensed into microdroplets and propelled toward target plant cells. The microdroplets penetrate the walls of the target cells, carrying the genetic material or other biological substance into the cells.

What is claimed is:

1. A method of introducing a biological substance into living target cells, the method comprising providing the biological substance in a liquid solution or suspension, and dispersing this liquid into microdroplets of sufficient size to penetrate the target cells without destroying the target cells, and propelling these microdroplets toward the target cells with sufficient kinetic energy to penetrate the target cells, wherein the liquid is dispersed into microdroplets by delivering the liquid into a rotating vessel which ejects the liquid through peripheral openings toward the target cells.

2. A method of introducing a biological substance into living target cells, the method comprising providing the biological substance in a liquid solution or suspension, and dispersing this liquid into microdroplets of sufficient size to penetrate the target cells without destroying the target cells, and propelling these microdroplets toward the target cells with sufficient kinetic energy to penetrate the target cells, wherein drops of the liquid are impacted by a rotating deflector to disperse the drops into microdroplets and propel the microdroplets toward the target cells.

3. A method of introducing a biological substance into living target cells, the method comprising providing the biological substance in a liquid solution or suspension, and dispersing this liquid into microdroplets of sufficient size to penetrate the target cells without destroying the target cells, and propelling these microdroplets toward the target cells with sufficient kinetic energy to penetrate the target cells, wherein the liquid is contained in a microprojectile which is propelled toward the target cells and stopped to eject the liquid from the microprojectile, dispersing the liquid into microdroplets and propelling the microdroplets toward the target cells.

* * * * *